United States Patent [19]

Rudolf

[11] Patent Number: 4,636,827
[45] Date of Patent: Jan. 13, 1987

[54] SEMICONDUCTOR DEVICE RESPONSIVE TO IONS

[75] Inventor: Felix Rudolf, Cortaillod (NE), Switzerland

[73] Assignee: Fondation Suisse de Recherche en Microtechnique, Neuchatel, Switzerland

[21] Appl. No.: 777,876

[22] Filed: Sep. 20, 1985

Related U.S. Application Data

[63] Continuation of Ser. No. 399,846, Jul. 19, 1982, abandoned.

[30] Foreign Application Priority Data

Jul. 24, 1981 [FR] France ................................ 81 14501

[51] Int. Cl.⁴ ..................... H01L 49/02; H01L 29/78; H01L 29/66; H01L 29/06
[52] U.S. Cl. .......................................... 357/25; 357/6; 357/23.1; 357/23.7; 357/55; 324/71.5; 204/1 T; 204/416; 204/418
[58] Field of Search .................... 357/23.7, 23.1, 23.6, 357/23.5, 25, 55, 6, 41; 324/71.5; 204/1 T, 416, 418

[56] References Cited

U.S. PATENT DOCUMENTS

| | | | |
|---|---|---|---|
| 3,258,663 | 6/1966 | Weiner | 357/23 TF |
| 4,020,830 | 5/1977 | Johnson et al. | 357/25 |
| 4,037,242 | 7/1977 | Gosney | 357/23 VT |
| 4,133,735 | 1/1979 | Afromowitz et al. | 357/25 |
| 4,180,771 | 12/1979 | Guckel | 357/25 |
| 4,218,298 | 8/1980 | Shimada et al. | 357/25 |
| 4,397,714 | 8/1983 | Janata et al. | 357/25 |

OTHER PUBLICATIONS

M. A. Afromowitz et al., "Fabrication of pH-Sensitive Implantable Electrode by Thick Film Hybrid Technology", *Journal of Bioengineering*, vol. 1 (1977), pp. 55–60.
M. Esashi et al., "Integrated Micro Multi Ion Sensor Using Field Effect of Semiconductor", *IEEE Transactions on Biomedical Engineering*, vol. BME-25 (1978), pp. 184–192.
J. N. Zemel, "Chemically Sensitive Semiconductor Devices", *Research/Development* vol. 28 (1977), pp. 38–44.

Primary Examiner—J. Carroll
Attorney, Agent, or Firm—Parkhurst & Oliff

[57] ABSTRACT

A device comprising a field effect transistor having a floating gate 20 formed on a first surface of a substrate 10 over gate oxide 13a and source and drain regions 11, 12. A responsive layer 15 is provided on the second surface of the substrate and is capacitatively coupled to the floating gate via a thin insulating membrane 13b at a location away from the transistor. The device is applicable in the biomedical domain.

8 Claims, 3 Drawing Figures

SEMICONDUCTOR DEVICE RESPONSIVE TO IONS

This is a continuation of application Ser. No. 399,846 filed July 19, 1982, now abandoned.

BACKGROUND

The present invention relates to semiconductor devices responsive to ions in general and is concerned more particularly with devices comprising a field effect transistor.

New devices have already been developed for detecting and measuring chemical properties, such as the activity of ions, of a liquid medium. Among these known devices is the ISFET transistor (Ion-Sensitive Field Effect Transistor) the structure and operation of which are described, for example, in U.S. Pat. No. 4,020,830. The ISFET transistor is a field effect transistor with an isolated gate, the gate of which is replaced with a conducting solution and the insulating layer of which reacts in a specific manner with certain ions in the solution. The response of the ISFET transistor is therefore dependent on the nature and concentration of the solution. One of the problems that exists with the known structures is to avoid interference between the solution and the purely electronic elements, namely the channel, source and drain regions, and the connections of the device. The present materials and techniques of encapsulation do not enable this disadvantage to be completely eliminated. Moreover, the responsive layer which is in contact with the solution and with the channel zone should be relatively thin, typically of the order of 0.1 micron, in order to ensure good operation of the transistor. Now, this responsive layer should also serve as a barrier to the migration of ions of the solution towards the electronic device, and it will be easily understood that this barrier becomes much less effective as its thickness is reduced.

One known method for avoiding interference between the solution and the drain and source contacts consists in providing deep diffusions across the substrate and making the drain and source connections on the back of the silicon chip. This method obtains the advantage of eliminating any connection zone on the surface which is in contact with the solution. However, the formation of these deep diffusions across the substrate is not compatible with the standard technological procedures and these diffusions are, moreover, fairly badly controlled.

BRIEF SUMMARY OF THE INVENTION

Accordingly, an object of the present invention is a semiconductor device of the field effect transistor type which is responsive to ions, and which does not have the disadvantages mentioned above.

According to the present invention, there is provided a semiconductor device adapted to respond selectively to the ions of a solution to which it is exposed and having a responsive layer and a field effect transistor constituted by a source region, a channel region and a drain region formed on a substrate and a gate separated from the source, channel and drain regions by an insulating layer. The said gate is floating and capacitatively coupled with the responsive layer at a location away from the source, channel and drain regions.

The field effect transistor is preferably provided on a first surface of the substrate while the responsive layer is formed on the second surface of the substrate.

In this manner the electronic part of the device is located on the opposite side of the substrate with respect to that which is in contact with the electrolyte. It is thus easier to effect isolation of this electronic part. Another advantage results from the capacitative coupling between the responsive layer and the floating gate. The dielectric of this coupling capacitor, which also serves as a barrier to migration of ions, can be relatively thick since its surface can be large. It is in fact the total value of the coupling capacitance that is important for correct operation of the device.

BRIEF DESCRIPTION OF THE DRAWINGS

The invention will now be described in more detail, by way of example, with reference to the accompanying drawings, in which.

DETAILED DESCRIPTION

Figure 1:
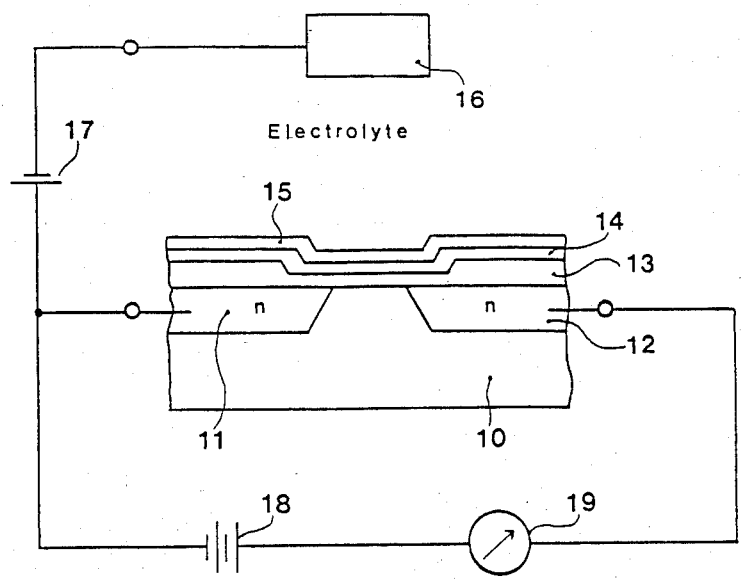
FIG. 1 shows a known FET transistor structure which is responsive to ions.

FIG. 1 illustrates the prior art and shows, in section, known FET transistor structure employed as an electrochemical transducer. This structure comprises a substrate 10 of doped p-type silicon, two separate n-type diffusion regions 11 and 12 forming respectively the source and the drain, an insulating layer 13, typically of $SiO_2$, a protective layer 14, for example of $Si_3N_4$, and a responsive layer 15. The responsive layer 15 is in contact with an electrolyte in which is immersed a reference electrode 16. The responsive layer 15 is provided for reacting with ions of a given type of the electrolyte, and producing an electrochemical surface potential which modulates the electrical field of the channel region. The surface potential depends on the extent of the reaction which in turn depends on the concentration of the ions of the given type in the electrolyte. Changes in this concentration produce variations of the conduction current measured by the ammeter 19.

In a structure such as that shown in FIG. 1, the contact zones of the drain and of the source (not shown) are located on the same side as the electrolyte which, having regard to the materials used for the encapsulation, does not enable the stability of the device to be ensured for a long period. Moreover, the thickness of the gate oxide 13 and of the protective layer 14 should be sufficiently small in the channel zone for the device to function correctly. Now, this small thickness also constitutes a disadvantage insofar as it reduces the efficacy of the protective layer 14.

Figure 2:
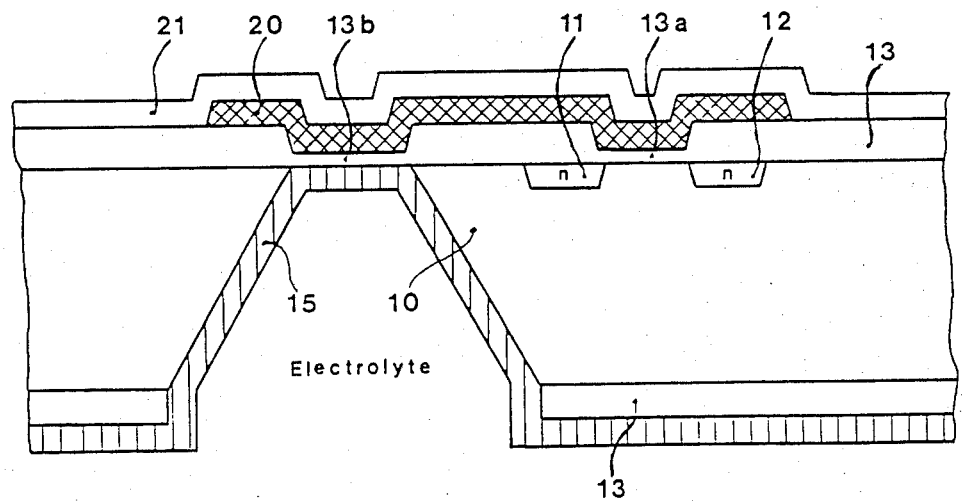
FIG. 2 shows a first arrangement responsive to ions in accordance with the principles of the present invention.

There is therefore provided according to the invention an FET transistor structure responsive to ions which incorporate a floating gate and in which the responsive layer is located opposite the floating gate. A structure in accordance with the principles of the invention is shown in FIG. 2 in which the elements that are analogous to those of FIG. 1 bear the same references. There is provided an FET transistor having a channel in a p-type substrate 10 of silicon, two n-type diffusion regions 11 and 12 constituting the source and the drain, and an insulating layer 13 of SiO₂ the reduced thickness part of which 13a constitutes the gate oxide. The gate 20, made for example of aluminum of doped polycrystalline silicon, is floating and is capacitatively coupled through a thin oxide layer 13b with the responsive layer 15. This reponsive layer 15 is located on the other surface of the silicon chip which has previously been subjected to attack in order to etch away the silicon oposite the thin oxide layer 13b. Thus, the insulating layer 13 of SiO₂ is interposed between the substrate 10 and the responsive layer 15 in order to reduce the influence of the electrolyte on the transistor. The structure also includes drain and source contact zones which are not shown because they are outside the plane of the section, but are located on the upper surface, that is to say on the surface opposite that which is in contact with the electrolyte. The upper surface is further coated with an insulating layer 21 which insulates the floating gate 20.

The oxide layer 13b, which serves as the dielectric of the capacitor formed by the floating gate 20 on the one hand and the responsive layer 15 on the other hand, may be thick provided that its surface is large, since it is the total value of the coupling capacitance that is important. It is then possible to produce an effective barrier which opposes the migration of the ions of the electrolyte towards the floating gate.

The silicon substrate 10 is an opaque material which consequently protects the transistor from all light that could reach the electrolyte. This results directly from the characteristics of the structure of the invention.

Figure 3:
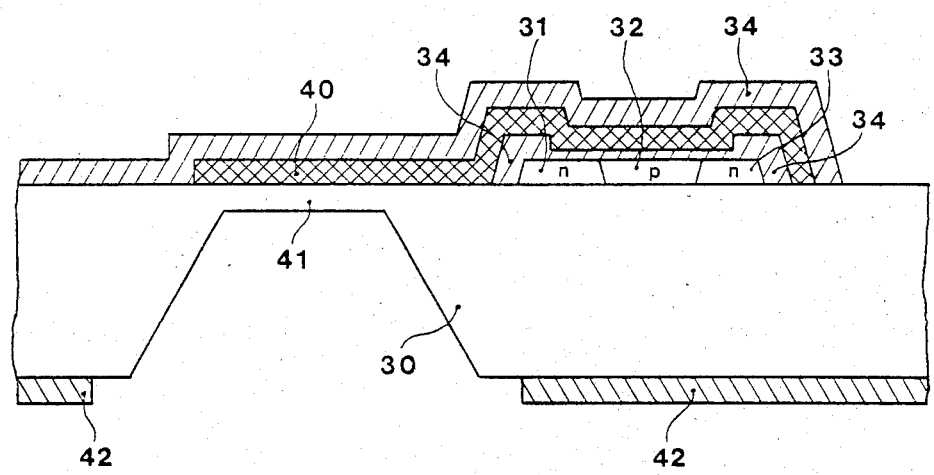
FIG. 3 shows a second arrangement responsive to ions in accordance with the principles of the present invention.

FIG. 3 shows, in section, another embodiment of the invention produced on an insulating substrate such as sapphire. On a sapphire substrate 30 there are produced, with the aid of conventional SOS (Silicon On Sapphire) technology three regions 31, 32 and 33 of doped silicon with alternate polarities and constituting respectively the source, the channel and the drain of the transistor. The floating gate 40 may be made of suitably doped polycrystalline silicon. An insulating layer 34 of SiO₂ covers the floating gate 40 as well as the source, channel and drain zones. The lower surface of the small sapphire substrate is locally eroded, for example, by ultrasonic energy, in such a manner as to form a membrane 41 having a thickness of about ten microns opposite the floating gate. This membrane 41 serves at one and the same time as a responsive layer, a barrier to ion migration and a dielectric of the coupling capacitor between the responsive layer and the floating gate. Such a device can be used as a pH sensor, the sapphire having a selective response to H⁻ ions. An opaque layer 42 can be deposited on the lower surface in order to suppress the action of light on the transistor.

In the case of a device provided on an insulating substrate and including a responsive layer 15 composed of a material different from that of the substrate, it is possible to provide this responsive layer on the same side as the electronic part. This responsive layer will, however, always be capacitatively coupled to the floating gate of the transistor in a region remote from the transistor zone.

The two constructional embodiments described above are given merely by way of example and it is clear that they do not limit the scope of the invention. Other known layers may be used to serve as a barrier to the ions. Si₃N₄ may be mentioned as an example of such layer materials. Materials other than those specified may be used for the structures according to the invention. Such materials are known for their electrochemical properties and have already been used as the responsive element. For example, aluminum or tantalum oxides, or glasses and ion exchanges in a PVC or photoresist matrix, may be used for such structures.

What is claimed is:

1. A semiconductor device for selective response to the ions of a solution to which it is exposed, said device comprising:
   a substrate having first and second surfaces;
   a responsive layer positioned in a recessed area in a first region of said substrate on said first surface of said substrate; and
   a field effect transistor positioned in a second region of said substrate separate from said first region and including a source region, a channel region and a drain region formed on said second surface of said substrate, and a gate separated from said source, channel and drain regions by an insulating layer to form said field effect transistor;
   said gate being electrically floating and laterally extending from said field effect transistor in said second region to said first region in such a manner that it is capacitively coupled to said responsive layer in said first region and separated therefrom so as to minimize ion migration between said solution and said gate, said first region being spaced apart from said second region.

2. The device of claim 1 wherein the capacitative coupling occurs across a thin membrane of an insulating material.

3. The device of claim 2, wherein the substrate is an insulating material.

4. The device of claim 3, wherein the membrane is a thin part of the substrate.

5. The device of claim 4, wherein the thin part of the substrate also constitutes the responsive layer.

6. A semiconductor device for selective response to the ions of a solution to which it is exposed, said device comprising:
   a semiconductor substrate having first and second surfaces, said first surface having a source, channel and drain region formed in a first portion of said first surface, and insulating layer deposited over said first surface and a gate deposited over said insulating layer such that said gate is electrically floating and forms a field effect transistor in said first portion of the substrate in combination with said source, channel and drain regions; and
   an ion responsive layer deposited on a recessed area of said second surface of said substrate and constructed and arranged to be capacitively coupled through said insulating layer to said gate in a second portion of said substrate separate from said first portion, said second portion of said substrate being spaced laterally apart from said first portion of said substrate in which said field effect transistor is defined;
   wherein said insulating layer deposited on said first surface extends such that it forms a gate oxide region of the transistor in said first portion and extends between said gate and ion responsive layer in said second portion to form a layer across which said capacitive coupling occurs, said insulating layer being of a thickness to serve as a barrier to the migration of said ions between said solution and said gate.

7. A semiconductor device for selective response to the ions of a solution to which it is exposed, said device comprising:

a substrate having first and second surfaces, said substrate having source, channel and drain regions deposited on said first surface on a first portion of said substrate, an insulating layer deposited over said source, channel and drain regions, and an electrically floating gate deposited over said insulating layer to form a field effect transistor in said first portion of said substrate in combination with said source, channel and drain regions; and an ion responsive layer formed on a recessed area of said second surface in a second portion of said substrate separate from said first portion and laterally spaced from said first portion, said floating gate extending from said first portion to said second portion such that said gate and ion responsive layer are capacitively coupled in said second portion, and separated so as to prevent ion migration between said solution and said gate.

8. The device of claim 7 wherein said ion responsive layer is formed by eroding the second surface of said substrate to form said ion responsive layer is said recessed area in said second portion.

* * * * *